(12) United States Patent
Eraly et al.

(10) Patent No.: US 10,010,431 B2
(45) Date of Patent: Jul. 3, 2018

(54) CUSTOMIZED SURGICAL GUIDE

(71) Applicant: Materialise N.V., Leuven (BE)

(72) Inventors: Koen Eraly, Kessel-Lo (BE); Frederik Gelaude, Herent (BE); Nadia Van Geel, Mechelen (BE); Jan Demol, Heverlee (BE)

(73) Assignee: Materialise N.V., Leuven (BE)

( * ) Notice: Subject to any disclaimer, the term of this patent is extended or adjusted under 35 U.S.C. 154(b) by 277 days.

(21) Appl. No.: 14/774,560

(22) PCT Filed: Mar. 27, 2013

(86) PCT No.: PCT/EP2013/056566
§ 371 (c)(1),
(2) Date: Sep. 10, 2015

(87) PCT Pub. No.: WO2014/154266
PCT Pub. Date: Oct. 2, 2014

(65) Prior Publication Data
US 2016/0030196 A1  Feb. 4, 2016

(51) Int. Cl.
*A61F 2/46* (2006.01)
*A61B 17/17* (2006.01)
(Continued)

(52) U.S. Cl.
CPC ........ *A61F 2/4612* (2013.01); *A61B 17/1739* (2013.01); *A61B 17/1778* (2016.11); *A61B 17/808* (2013.01); *A61B 2017/568* (2013.01); *A61B 2034/108* (2016.02); *A61F 2/30942* (2013.01); *A61F 2002/4629* (2013.01); *A61F 2002/4687* (2013.01)

(58) Field of Classification Search
CPC ............... A61F 2/4612; A61B 17/1739; A61B 17/1778; A61B 2034/108
See application file for complete search history.

(56) References Cited

U.S. PATENT DOCUMENTS 5,741,266 A * 4/1998 Moran ............... A61B 17/1725
606/104
5,769,856 A * 6/1998 Dong .................... A61F 2/4081
606/80

(Continued)

FOREIGN PATENT DOCUMENTS

EP        2491873 A2    8/2012
WO    WO2012058344 A1  5/2012
(Continued)

*Primary Examiner* — Christian Sevilla
(74) *Attorney, Agent, or Firm* — Rudy J. Ng; Bret E. Field; Bozicevic, Field & Francis LLP (57) ABSTRACT

Customized surgical guide for guiding a bone implant to a predetermined location on the bone during a surgical procedure, wherein the guide comprises a body comprising at least one implant contacting surface and at least one patient specific bone contacting surface, wherein the implant contacting surface is arranged to contact the implant for ensuring a unique and stable fit between the guide and the implant, and wherein the bone contacting surface is arranged to contact the bone for ensuring a unique and stable fit of a combination of the guide and the implant on the predetermined location on the bone.

20 Claims, 6 Drawing Sheets

(51) Int. Cl.
*A61F 2/30* (2006.01)
*A61B 17/80* (2006.01)
*A61B 17/56* (2006.01)
*A61B 34/10* (2016.01)

(56) References Cited

U.S. PATENT DOCUMENTS

| | | | | |
|---|---|---|---|---|
| 5,895,390 A * | 4/1999 | Moran | ............... | A61B 17/1725 606/104 |
| 2004/0230197 A1 * | 11/2004 | Tornier | ............. | A61B 17/1778 606/87 |
| 2008/0243127 A1 * | 10/2008 | Lang | ................... | A61B 5/4528 606/87 |
| 2009/0164021 A1 * | 6/2009 | Dallmann | ................ | A61F 2/40 623/19.11 |
| 2010/0191246 A1 * | 7/2010 | Howald | .................... | A61F 2/34 606/91 |
| 2010/0191340 A1 * | 7/2010 | Dreyfuss | ............ | A61B 17/1684 623/19.11 |
| 2010/0268238 A1 * | 10/2010 | Sikora | ................ | A61B 17/1684 606/87 |
| 2011/0130795 A1 * | 6/2011 | Ball | ................... | A61B 17/1778 606/86 R |
| 2012/0041446 A1 * | 2/2012 | Wong | .................. | A61B 17/1703 606/96 |
| 2012/0053586 A1 * | 3/2012 | Kiritsis | .............. | A61B 17/8061 606/71 |
| 2012/0053587 A1 * | 3/2012 | Kiritsis | .................. | A61B 17/17 606/71 |
| 2012/0109137 A1 * | 5/2012 | Iannotti | .............. | A61B 17/1728 606/87 |
| 2012/0123423 A1 * | 5/2012 | Fryman | .................. | A61B 17/15 606/89 |
| 2012/0296339 A1 * | 11/2012 | Iannotti | .................. | A61B 17/15 606/87 |
| 2013/0110116 A1 * | 5/2013 | Kehres | ............... | A61B 17/1739 606/96 |
| 2013/0172898 A1 * | 7/2013 | Iannotti | .............. | A61B 17/1739 606/102 |
| 2013/0236874 A1 * | 9/2013 | Iannotti | .................. | B29C 39/02 434/274 |
| 2014/0257304 A1 * | 9/2014 | Eash | .................. | A61B 17/1778 606/87 |

FOREIGN PATENT DOCUMENTS

| | | | | |
|---|---|---|---|---|
| WO | WO2012151393 A2 | 11/2012 | | |
| WO | WO 2012166888 A2 * | 12/2012 | ........... | A61F 2/4609 |
| WO | WO2012166888 A2 | 12/2012 | | |

* cited by examiner

CUSTOMIZED SURGICAL GUIDE

The present invention relates to a customized surgical guide, a method for providing such a guide and method for placing an implant on a predetermined location on the bone.

The success rate of the a surgical procedure of implanting a bone implant, for instance for reconstructing joints or for repairing defects in the bone, is largely dependent on the accuracy of the placement of the implant. Already a minor misplacement can result in diminished functionality of the implant, for instance in terms of freedom of movement, muscle tensioning and/or stability of the joint.

According to more recent developments, the exact location of the implant on the bone is determined pre-operative. It is then however sometimes still difficult for a surgeon to place the implant on this predetermined location. It is for instance possible that when the implant is placed on the bone, the implant appears to exactly fit the bone, while this is not the case. This may even happen when implanting customized implants which are formed complementary to the bone surface on which they are planned to be placed.

This misplacement of the implants may for instance be due to the limited visibility on the bone as the surgeon usually tries to uncover as little bone as possible and to reduce the number and extent of cuts.

It is therefore a goal of the current invention, amongst other goals, to at least partly solve this problem.

This goal, amongst other goals, is met by a customized surgical guide according to claim 1. More specifically, this goal, amongst other goals, is met by a customized surgical guide for guiding a bone implant to a predetermined location on the bone during a surgical procedure, wherein the guide comprises a body comprising at least one implant contacting surface and at least one patient specific bone contacting surface, wherein the implant contacting surface is arranged to contact the implant for ensuring a unique fit between the guide and the implant, and wherein the bone contacting surface is arranged to contact the bone for ensuring a unique fit of a combination of the guide and the implant on the predetermined location on the bone. The guide facilitates the placement of an implant on the predetermined location which is otherwise difficult to place accurately. It is for instance possible that the implant alone does not have a unique fit on the bone. By combining such an implant with a guide according to the invention, it is ensured that the combination of the guide and implant have a unique and stable fit on the bone, such that the implant is accurately positioned on the predetermined location. The chance of misplacements is hereby minimized or misplacements can even be prevented.

It should be noted that with a unique fit between two elements, for instance the combination of the implant and guide with the bone, is meant that one element can only be placed with a stable and durable fit, taking deviations in manufacturing and/or measuring into consideration, on the other element. The surfaces are preferably chosen such that when the elements are placed otherwise, the fit will not be stable, which can for instance be noticed by substantial play, for instance wobbling, between the elements. It is possible that surfaces are hereto also chosen such that when the elements are placed otherwise, misalignment can be detected visually and/or with touch.

The bone contacting surface of the guide hereby has the function to ensure a stable fit of the combination of the guide and implant on the bone. The patient specific bone contacting surface is hereto preferably formed at least partially complementary to a bone surface to allow the stable and unique fit. The bone contacting surface is hereby preferably arranged to complement the bone surface, within a range of deviations due to manufacturing and/or measurement. It should be noted that it is not necessary that the bone contacting surface is formed complementary to a large surface of the bone. It is sufficient that the bone contacting surface comprises sufficient contact points or lines for allowing a stable placement of the combination on the bone. The bone contacting surface of the guide, preferably in combination with a bone contacting surface of the implant, hereby provides a stable placement on the bone such that other functions can be carried out efficiently, such as drilling holes and/or fixing the implant to the bone as will be explained in more detail below.

The form of the bone contacting surface can be based on a preferably digital three-dimensional model of the bone, preferably including the implant, for instance obtained by imaging as will be discussed in more detail below. The location of the bone surface, and thereby the bone contacting surface, is to that extent important that a balance must be found between a stable fit of the guide, for which a larger distance from the predetermined location is preferred, and a guide with a compact configuration, for which a smaller distance from the predetermined location is preferred.

Preferably the body comprises a plurality of bone contacting surfaces to further improve the ease of placement of the combination. The bone contacting surfaces are preferably located at positions surrounding the implant to improve the stability.

The implant contacting surface on the other hand has the function to ensure a unique fit between the implant and the guide. As the bone contacting surface ensures a unique fit on the bone, also the position of the implant with respect to the guide is critical. The implant contacting surface hereby engages the implant and enables a stable fit of the guide onto the implant. Also the implant contacting surface can thereto be formed at least partially complementary to a surface of the implant for ensuring the unique fit. The implant may for instance be provided with a surface structure comprising rims and/or grooves, wherein the implant contacting surface of the guide is formed with an at least partly complementary formed surface to ensure the unique fit. It is also possible that the implant is a customized implant also having a patient specific surface facing away from the bone. The implant contacting surface can then be manufactured to at least partially complement this surface.

The body of the guide preferably is a single unit, i.e. manufactured in one piece, comprising the bone contacting surfaces and implant contacting surfaces. At least a part of the outer surface of the body of the guide hereby forms these surfaces. It is however also possible that the guide comprises several parts, which are for instance moveable with respect to each other. By moving the parts, the guide can be customized to the patient and/or implant. After customisation, the parts can be locked.

According to a preferred embodiment, the bone contacting surface of the guide is arranged such that a combination of a bone contacting surface of the implant and said bone contacting surface of the guide together ensure the unique fit. According to this embodiment, the combination of the bone contacting surfaces of the implant and the guide provide the stable and unique fit. The guide alone, i.e. without implant, would thereby not have the unique fit. By also using the contact surface of the implant, which by itself may not provide a unique fit on the bone, the size and/or complexity of the bone contacting surface of the guide can be reduced.

It is however also possible that the bone contacting surface of the guide is arranged for ensuring a unique fit of the guide on the bone, preferably at or near the predetermined location. In this embodiment, the guide on its own provides a unique and stable fit on the bone, such that the design of the implant is less critical. For instance, even in combination with a generic implant, i.e. not customized to the patient, the customized guide then still provides an accurate placement of said implant on the predetermined location via the accurate placement of the guide.

An accurate placement of the guide, and thereby the implant on the predetermined location, on the bone is of particular importance to ensure correct fixation of the implant to the bone. More specifically, being able to accurately insert bone screws along preferably pre-operatively planned screw trajectories significantly increases the success rate of the surgical procedure. These screw trajectories can be determined pre-operatively based on the three-dimensional model of the bone, preferably in combination with the implant. The optimal trajectories can then be determined, for instance based on the quality of bone and the optimal direction of forces for ensuring optimal loading conditions in use. The implant may already be provided with holes aligned in accordance with the pre-operatively planned screw trajectories for receiving bone screws and/or drills. The guide then ensures that the implant is placed as pre-operatively planned, such that also the holes are aligned with the planned trajectories.

It is possible that the guide leaves these screw holes free, such that the guide does not cover the implant at a location of a screw hole. However, according to a further preferred embodiment, the guide comprises means for guiding screws and/or drills for fixing the implant to bone. These means are preferably arranged to guide the screws along the pre-operatively planned screw trajectories and/or to guide a drill for drilling a screw hole in the bone along said planned trajectories.

A further preferred embodiment comprises a hole aligned with a screw hole in said implant. The hole may be a screw hole for receiving a screw with a head for fixing the implant to the bone, wherein the diameter of the screw hole in the guide is equal to or larger than the diameter of the screw hole of the implant such that the head of the screw is received in the screw hole of the guide and engages the implant. This allows the implant to be fixed to the bone without fixing the guide to the bone. It is therefore possible to fix the implant to the bone using suitable bone screws without removing the guide. This has the advantage that the guide provides stability while inserting the screws. When the implant is sufficiently fixed to the bone, the guide can be removed, as the head of the screw is received in the screw hole. The diameter of the screw hole of the guide is hereto equal to or larger than the diameter of the head of the screw, whereas the diameter of the screw hole in the implant is smaller than the diameter of the head of screw such that the head engages said implant.

In order to provide guidance to the screw when the screw is inserted, the guide is preferably provided with a flange or rim surrounding the screw hole and wherein the inner diameter of said flange and the diameter of said screw hole have a diameter corresponding to the diameter of the head of the screw for guiding the screw. The guiding surface formed by the screw hole and the associated flange hereby restricts movement of the screw. The length of the surface, seen in the direction of insertion of the screw, preferably corresponds to the length of the screw, seen from the surface of the bone.

In particular when long screws are used, it is advantageous when the flange is removably connected to the guide. The flange and the guide can thereto be provided with suitable connecting means such as threading. It is also possible that the flange is removably connected to the implant, wherein the flange in connected state extends through a corresponding hole in the guide. The flange can for instance be formed as a screw cylinder which can be threaded on the guide and/or the implant. The hole in the guide and/or the screw hole in the implant can thereto be threaded for receiving a threaded element, for instance a screw cylinder and/or drill cylinder as will be discussed below. This also temporality interconnects the implant and the guide.

In order to be able to drill holes for the above mentioned screws, the guide further preferably comprises a removable drill guide for guiding a drill for drilling a screw hole in the bone for said screw, preferably along the pre-operatively planned trajectories, wherein the drill guide preferably has a cylindrical shape with a varying outer diameter corresponding to the diameters of the screw holes of the guide and the implant for insertion of the drill guide in said holes, wherein the drill guide has an inner diameter smaller than the diameter of the screw hole in the implant. The outer surface of the cylindrical drill guide conforms to the inner surfaces of the screw holes of the guide and implant, such that the drill guide is held firmly upon insertion. As said, the outer surface can be provided with threading cooperating with threading in the hole of the implant and/or the surgical guide. The inner diameter of the drill guide is preferably constant and corresponds to the diameter of the used drill, which is typically smaller than the diameter of the thread of the screw.

Although it is possible to use the same drill guide, or a plurality of separate drill guides, in the form as a drill cylinder as described above for several screw holes in the guide and the implant, it is also possible to use a custom made drill guide arranged to uniquely fit the implant and/or the surgical guide, wherein the drill guide engages a plurality of screw holes for guiding a drill therein. By placing this custom drill guide, the surgeon can efficiently drill each of the necessary holes and simply remove the drill guide when he is done.

It is however also possible that the surgical guide according to the invention is used as a drill guide. The hole in the guide is then a drill hole for receiving and guiding a drill, wherein the diameter of the drill hole is smaller than the diameter of the screw hole of the implant. After drilling of the hole, or preferably plurality of holes, the surgical guide is removed and the screws can be inserted.

As said, it is preferred if the location and/or the trajectory of the screw and/or drill hole is planned pre-operatively, for instance based on the three-dimensional model.

In particular when the guide according to the invention is to be used for drilling holes and/or fixing screws, it is important that the guide provides a stable placement of the combination of the implant and the guide on the bone. It is therefore preferred if the bone contacting surface, or a plurality of bone contacting surfaces, of the guide, preferably in combination with the bone contacting surface(s) of the implant, are arranged such that the bone contacting surface(s) provide(s) a stable support. More preferably, the bone contacting surface hereto at least partially surrounds and extends outwardly of the screw/drill guiding means of the guide, seen in a direction perpendicular to the fixation direction.

According to a further preferred embodiment the bone contacting surface and the implant contacting surface are located on a bone facing side of the body of the guide facing the bone in connected state. In connected state, i.e. wherein the combination of the guide and implant are placed and are in contact with the bone, at least a part of the implant is located between the guide and the bone. This allows easy removal of the guide after proper placement and perhaps fixation of the implant as discussed above.

Although it is possible to first place the implant on the bone and to subsequently place the guide for ensuring the unique fit, according to a further preferred embodiment, the guide is arranged to contact the implant such that after combining the guide and the implant, the combination of the guide and implant can be uniquely fitted on the bone. Before placement of the implant on the bone, the guide is combined with the implant such that the combination of the implant and guide is uniquely fitted to the bone. In other words, the combination of the guide and implant can preferably be placed on the bone with a unique fit in a single action.

To be able to ensure easy handling of the combination of the guide and the implant during placement of the combination on the bone, a further preferred embodiment comprises interconnecting means for temporarily interconnecting the guide and the implant during the surgical procedure. The guide is hereby removably connected to the implant, such that after proper placement of the implant, preferably after fixing said implant to the bone as explained above, the guide can be removed from the implant.

An efficient interconnection can be achieved by a screw connection, for instance in the form of the screw/drill guiding means as discussed above. The guide can hereto be provided with a hole for receiving a screw which is aligned with a corresponding hole in the implant. The hole in de implant may for instance be threaded or it is possible that the hole in the implant at a location opposite the guide, for instance at or near the bone contacting surface, is widened for receiving a threaded element, for instance similar to a bolt. Upon removal of the guide, the screw is removed from the combination, thereby loosening the guide from the implant.

An efficient interconnection can also be achieved by a snap-fit connection. The guide and/or the implant may hereto be provided with a resilient member for engaging a surface of the other element. It is for instance possible that the guide comprises a resilient lip for engaging around an edge of the implant for interconnecting the guide and the implant. It is also possible that a resilient element is received in a corresponding hole of the other element.

To further facilitate the placement of the combination of the guide and the implant, a further preferred embodiment comprises positioning means arranged to facilitate positioning of the combination of the guide and implant on the bone, wherein the positioning means are arranged to engage at least one landmark bone feature, preferably near the predetermined location, on the bone. The positioning means have the function of providing an easy reference point to the surgeon such that the placement of the combination is easier. To further ensure the proper placement with respect to this landmark features, it is preferred that the positioning means comprise at least one patient specific positioning surface arranged to contact a surface of said landmark bone feature. This patient specific surface may for instance be formed at least partially complementary to said surface of said landmark bone feature.

That the feature should preferably be chosen near the predetermined location should not be interpreted too narrow. The landmark bone features do not need to be in the direct vicinity of the predetermined location. However, these landmark features should also not be chosen to far away such that for instance additional uncovering of bone is necessary. In this respect it is noticed that it is even possible that the positioning means are arranged to contact a feature, such as a bone feature for stable support, without uncovering said feature. It is also possible that a separate cut is made, next to the cut for placing the implant, for uncovering a landmark bone feature.

The positioning means can be used in addition to the bone contacting surface of the guide. It is however also possible that the patient specific positioning surface also functions as bone contacting surface in the sense of the invention. This leads to a simplified design.

In case of a glenoid implant, said land mark bone features are features around said glenoid, for instance chosen from the group consisting of the glenoid neck, the coracoid's base, coracoid's tip, the glenoid surface, the lateral border or 'margo lateralis' of the scapula, the acromion, and the glenoid rim.

For the case where the customized surgical guide is indeed for a glenoid implant, the body preferably comprises a flange section provided with a bone contacting surface arranged for contacting the lateral border of the scapula for ensuring the unique fit. The guide may also, or instead, be provided with a bone contacting surface or a surface of the positioning means, for contacting a bone surface chosen from the group consisting of the glenoid neck, the coracoid's base, coracoid's tip, the glenoid surface, the acromion and the glenoid rim.

The handling of the combination is further improved, without increasing the size of the implant, if the guide comprises a handle extending from the body. The handle can be used for manual operation of the surgeon for placement of the combination. As the guide is preferably removable from the implant, the relative large handle is removed from the patient upon removal of the guide from the implant. It is however also possible that the handle is removably attached to the guide, for instance using threading.

The invention further relates to a combination of a customized surgical guide according to the invention and a bone implant arranged to be implanted on the predetermined location on the bone. The implant can for instance be provided with the corresponding screw holes, for instance with threading, or elements for cooperation with the interconnecting means as described above. It is further possible that the implant comprises a plurality of separate pieces, together forming the implant.

As already discussed above, the guide is in particular advantageous in combination with an implant having a plurality of possible fits at or near the predetermined location, i.e. for implants lacking a unique fit on the bone. Without the use of a customized guide according to the invention, it is very difficult for a surgeon to accurately place the implant on the predetermined location, as the surgeon has little or no feedback on the accuracy of the placement. As the guide according to the invention provides a unique and stable fit, the combination can only be placed at one possible position, such that misplacements are prevented. The guide can furthermore provide sufficient support such that the surgeon can carry out other functions, such as drilling screw holes, preferably along pre-operatively planned trajectories, or inserting screws for fixing the implant to the bone.

The guide according to the invention can however also be used with implants having such a unique fit, for instance customized implants. By providing such an implant with a guide according to the invention, placement of the implant is made easier for the surgeon, in particular when the guide is provided with the positioning means and/or a handle as described above. The guide with the bone contacting surface hereby provides stability, as explained above.

The invention further relates to a method for providing a customized surgical guide for guiding a bone implant to a predetermined location on the bone of a patient during a surgical procedure, wherein the method comprises the steps of:
  providing a three-dimensional model of the bone at least at and near the predetermined location;
  identifying on the model at least one bone surface which ensures a unique and stable fit of a combination of the guide and the implant on the predetermined location on the bone; and
  designing the guide, wherein the guide comprises a body comprising at least one implant contacting surface and at least one patient specific bone contacting surface, wherein the implant contacting surface is arranged to contact the implant for ensuring a unique and stable fit between the guide and the implant, and wherein the bone contacting surface is arranged to contact the identified surface of the bone for ensuring the unique fit of the combination on the bone.

The preferably digital three-dimensional model contains surface information of the bone at the location of the implant and preferably also contains the design of the implant itself, including surface information thereof. The model most preferably comprises information of the implant positioned on the bone. The design of the implant, including the position of any screw holes, and/or the planning of the trajectories of said screws may also be based on the three-dimensional data of the bone. It is also possible that the implant is a generic implant.

From this model a, or a plurality of, patient specific suitable bone surface(s) is selected which can provide the unique stable fit to the combination of the guide to be designed and the implant. The step of identifying the bone surface may for instance include selecting surfaces of bone parts having sufficient supporting capacity, for instance by selecting parts having a high bone mineral density, parts without defects, surfaces having suitable geometrical properties for support, easy accessible surfaces by touch and/or vision and/or multiple surfaces resulting in a stable fit for the guide. Also the ability to provide guidance during placement may play a role in selecting suitable surfaces. A bone surface may for instance be selected if it provides good indication of correct placement of the combination, while the contribution to the actual support of the combination is limited.

As discussed above, the implant contacting surface is preferably formed at least partially complementary to the surface of the implant. Also the bone contacting surface is preferably formed at least partially complementary to the identified surface of the bone.

The implant contacting surface can be designed based on the design of the implant which is preferably also available. The implant contacting surface can then be designed to be at least partially complementary to this surface. It is however also possible that a generic implant contacting surface is designed, for instance for the case if the surfaces facing and contacting the guide are generic, which may also be the case for customized implants.

According to a preferred embodiment, the method comprises the step of identifying a bone contacting surface of the implant with which the implant contacts the bone, wherein the step of identifying the bone surface comprises identifying a bone surface which together with the bone contacting surface of the implant ensures the unique fit. In this embodiment, as explained above, the combination of the bone contacting surfaces of the implant and the guide provide the unique fit. The bone contacting surface of the implant can for instance be derived from the model, which preferably also contains the three-dimensional design of the implant.

However, as already discussed above, it is also possible that the step of identifying the bone surface comprises identifying on the model at least one bone surface which ensures a unique fit of the guide on the bone, preferably at or near the predetermined location on the bone. The guide itself is hereby responsible for providing the unique fit, such that that the design of implant is less critical.

As the alignment of the screws for fixing the implant along pre-operatively planned screw trajectories is of importance as already discussed above, according to a further preferred embodiment the step of designing the guide further comprises designing screw and/or drill guiding means for guiding screws and/or drills along pre-operatively planned screw trajectories. The guiding means can then be designed such that the screws can inserted accurately along the pre-operatively planned screw trajectories. The guiding means for instance include a simple hole, flange, screw cylinder and/or drill cylinder as discussed above.

A further preferred embodiment of the method further comprises the step of identifying at least one landmark bone feature on the bone in model, preferably near the predetermined location, wherein the step of designing the guide further comprises designing positioning means arranged to facilitate positioning of the combination of the guide and implant on the bone, wherein the positioning means are arranged to engage the landmark bone feature. As discussed above, these positioning means help the surgeon orientating the combination of the guide and implant and thereby facilitate accurate placement thereof. To further improve the stability of the combination as discussed above, the positioning means preferably comprise at least one patient specific positioning surface formed at least partially complementary to a surface of said landmark bone feature.

According to a preferred embodiment, the implant is a shoulder implant, wherein the step identifying a bone surface comprises identifying a bone surface on the lateral side of the scapula, wherein the step of designing the guide further comprises providing the body with a flange section provided with a bone contacting surface arranged for contacting the identified bone surface. The bone surface may for instance be chosen from the group consisting of the glenoid neck, the coracoid's base, coracoid's tip, the glenoid surface, the acromion, the later border and the glenoid rim.

According to a preferred embodiment, the step of providing the three-dimensional model comprises the step of obtaining an image of the bone. Digital patient-specific image information can be provided by any suitable means known in the art, such as for example a computer tomography (CT) scanner, including Cone Beam CT, a magnetic resonance imaging (MRI) scanner, an ultrasound scanner, or a combination of Roentgenograms. A summary of medical imaging has been described in "Fundamentals of Medical imaging", by P. Suetens, Cambridge University Press, 2009.

For example, the step of obtaining an image of the bone may for example comprise the steps of obtaining 2D datasets of the bone and reconstructing a 3D virtual bone model from said 2D datasets. Indeed, the first step in a planning is the construction of a 3D virtual model of the bone. This reconstruction starts with sending a patient to a radiologist for scanning, e.g. for a scan that generates medical volumetric data, such as a CT, MRI scan or the like. The output of the scan can be a stack of two-dimensional (2D) slices forming a 3D data set. The output of the scan can be digitally imported into a computer program and may be converted using algorithms known in the field of image processing technology to produce a 3D computer model of a relevant bone. Preferably, a virtual 3D model is constructed from the dataset using a computer program such as Mimics™ as supplied by Materialise N.V., Leuven, Belgium. Computer algorithm parameters are based on accuracy studies, as for instance described by Gelaude at al. (2008; Accuracy assessment of CT-based outer surface femur meshes Comput. Aided Surg. 13(4): 188-199). A more detailed description for making a perfected model is disclosed in U.S. Pat. No. 5,768,134 entitled 'Method for making a perfected medical model on the basis of digital image information of a part of the body'. Once the three-dimensional model of the bone is used to position the implant and optionally used for implant design, for instance by using a joint reconstruction method as disclosed in Gelaude et al. (2007; Computer-aided planning of reconstructive surgery of the innominate bone: automated correction proposals Comput. Aided Surg. 12(5): 286-94), the model can be used to identify suitable bone surfaces for supporting the guide.

The invention furthermore relates to a method for manufacturing a customized surgical guide comprising the steps of:
  providing a customized surgical guide according to the invention; and
  manufacturing said guide, preferably by using a three-dimensional printing technique, also referred to as rapid manufacturing technique, layered manufacturing technique, additive manufacturing technique or material deposition manufacturing technique.

Rapid manufacturing includes all techniques whereby an object is built layer by layer or point per point by adding or hardening material (also called free-form manufacturing). The best known techniques of this type are stereolithography and related techniques, whereby for example a basin with liquid synthetic material is selectively cured layer by layer by means of a computer-controlled electromagnetic beam; selective laser sintering, whereby powder particles are sintered by means of an electromagnetic beam or are welded together according to a specific pattern; fused deposition modelling, whereby a synthetic material is fused and is stacked according to a line pattern; laminated object manufacturing, whereby layers of adhesive-coated paper, plastic, or metal laminates are successively glued together and cut to shape with a knife or laser cutter; or electron beam melting, whereby metal powder is melted layer per layer with an electron beam in a high vacuum.

In particular embodiments, Rapid Prototyping and Manufacturing (RP&M) techniques, are used for manufacturing the guide of the invention. Rapid Prototyping and Manufacturing (RP&M) can be defined as a group of techniques used to quickly fabricate a physical model of an object typically using three-dimensional (3-D) computer aided design (CAD) data of the object. Currently, a multitude of Rapid Prototyping techniques is available, including stereo lithography (SLA), Selective Laser Sintering (SLS), Fused Deposition Modeling (FDM), Selective Laser Melting (SLM), foil-based techniques, etc. A common feature of these techniques is that objects are typically built layer by layer.

Stereo lithography (SLA), presently the most common RP&M technique, utilizes a vat of liquid photopolymer "resin" to build an object a layer at a time. On each layer, an electromagnetic ray, e.g. one or several laser beams which are computer-controlled, traces a specific pattern on the surface of the liquid resin that is defined by the two-dimensional cross-sections of the object to be formed. Exposure to the electromagnetic ray cures, or, solidifies the pattern traced on the resin and adheres it to the layer below. After a coat had been polymerized, the platform descends by a single layer thickness and a subsequent layer pattern is traced, adhering to the previous layer. A complete 3-D object is formed by this process.

Selective laser sintering (SLS) uses a high power laser or another focused heat source to sinter or weld small particles of plastic, metal, or ceramic powders into a mass representing the 3-dimensional object to be formed.

Fused deposition modeling (FDM) and related techniques make use of a temporary transition from a solid material to a liquid state, usually due to heating. The material is driven through an extrusion nozzle in a controlled way and deposited in the required place as described among others in U.S. Pat. No. 5,141,680.

Selective laser melting (SLM) is an additive manufacturing process that uses 3D CAD data as a digital information source and energy in the form of a high powered laser beam (usually an ytterbium fiber laser) to create three-dimensional metal parts by fusing fine metallic powders together. This method is described for instance in DE 19649865.

Foil-based techniques fix coats to one another by means of gluing or photo polymerization or other techniques and cut the object from these coats or polymerize the object. Such a technique is described in U.S. Pat. No. 5,192,539.

Typically RP&M techniques start from a digital representation of the 3-D object to be formed, in this case the design of the guide. Generally, the digital representation is sliced into a series of cross-sectional layers which can be overlaid to form the object as a whole. The RP&M apparatus uses this data for building the object on a layer-by-layer basis. The cross-sectional data representing the layer data of the 3-D object may be generated using a computer system and computer aided design and manufacturing (CAD/CAM) software.

The customized surgical guide of the invention may be manufactured in different materials. Typically, only materials that are biocompatible (e.g. USP class VI compatible) with the human body are taken into account. Preferably the guide is formed from a heat-tolerable material allowing it to tolerate high-temperature sterilization. In the case SLS is used as a RP&M technique, the surgical template may be fabricated from a polyamide such as PA 2200 as supplied by EOS, Munich, Germany or any other material known by those skilled in the art may also be used.

The invention furthermore relates to a method for placing a bone implant on a predetermined location on the bone during a surgical procedure, wherein the method comprises the steps of:
  providing a bone implant;
  providing a customized surgical guide according to the invention for guiding said bone implant;
  interconnecting said implant and said guide;
  placing said combination of the implant and the guide on the predetermined location on the bone;

With the guide according to the invention, the implant can be placed accurately and efficiently on the predetermined location. Preferably, the method further comprises the step of connecting said implant to the bone, for instance using screws as discussed above. The method can further comprise the step of drilling holes for said screws, preferably using the drill guide as discussed above. It is advantageous that the fixation of the implant, and the drilling of holes, can take place while the guide is still connected to the implant for stability. When the implant is for instance sufficiently fixed to the bone, the guide can be removed from the implant. It is however also possible that the surgical guide also functions as drill guide. After drilling of the holes in the bone, preferably as planned pre-operative, the guide is removed and the implant can be fixed.

The present invention is further illustrated by the following Figures, which show a preferred embodiment of the device according to the invention, and are not intended to limit the scope of the invention in any way, wherein.

Figure 1A:
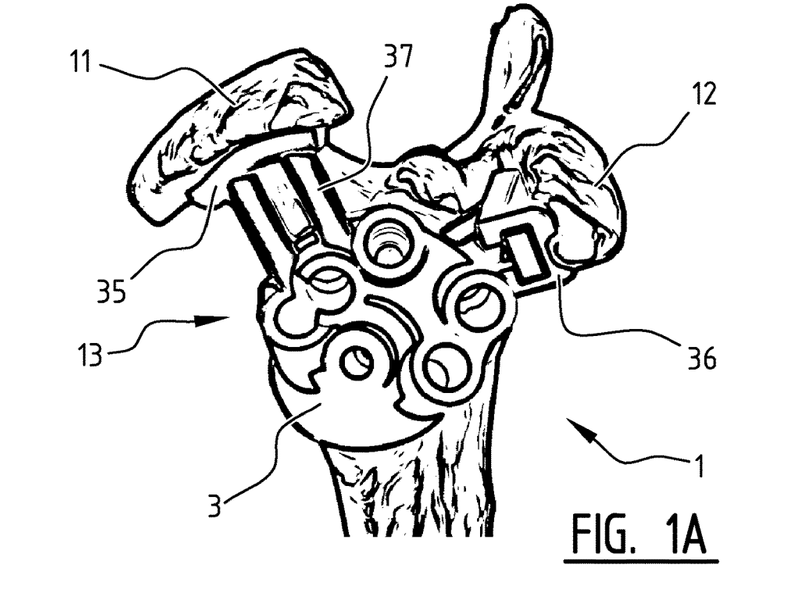
FIG. 1a schematically shows the shoulder blade with a correctly placed combination of an implant and guide according to the invention.
Figure 1B:
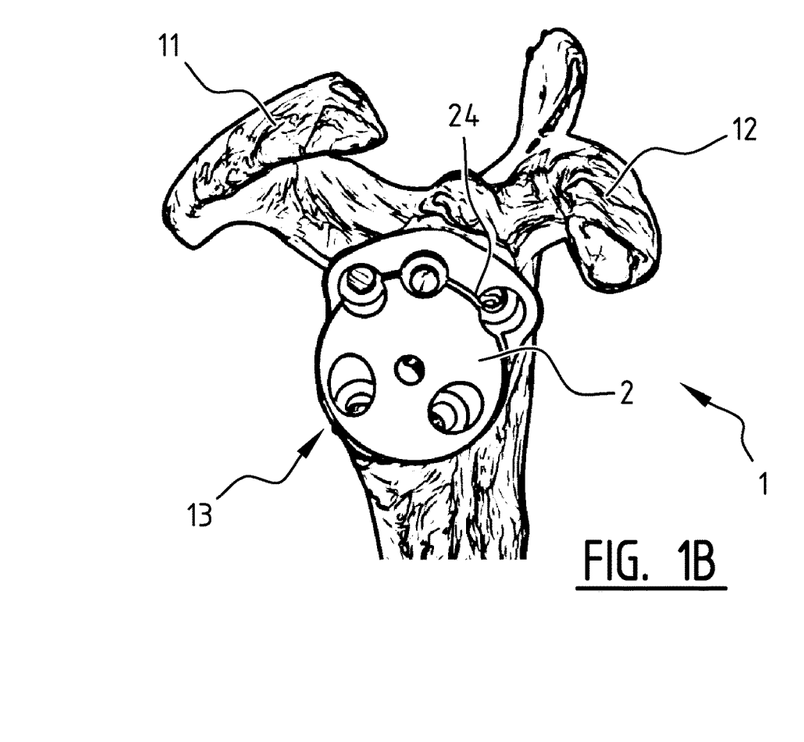
FIG. 1b schematically shows the implant of FIG. 1.
Figure 2A:
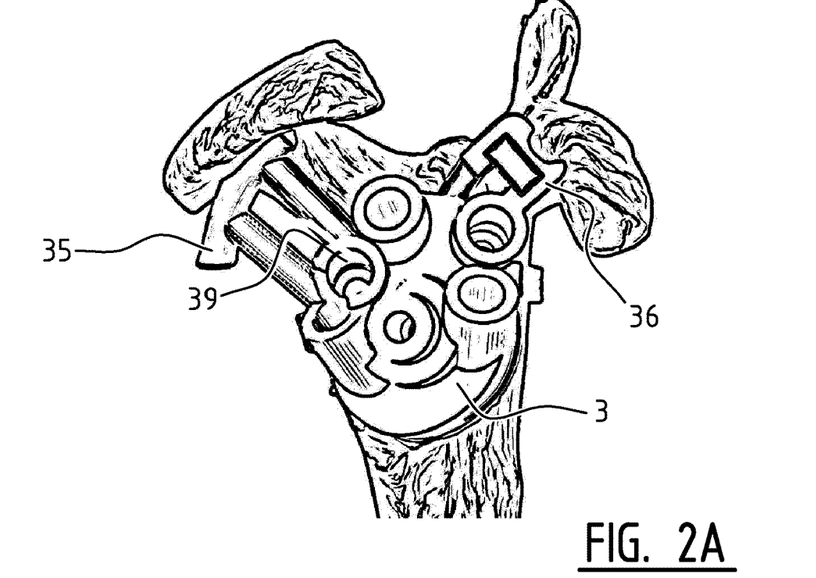
FIGS. 2a and 2b correspond to FIGS. 1a and 1b with the combination, respectively implant, being misplaced.

FIGS. 1a and 2a show a combination of the surgical guide 3 and an implant 2 placed on a bone 1, in this example at a shoulder. The guide 3 is arranged to facilitate correct placement of the implant 2 on the bone 1, as the placement of an implant 2 on the bone 1 is critical. The view of FIGS. 1b and 2b correspond to the views of FIGS. 1a and 1b without the guide 3 according to the invention.

Figure 2B:
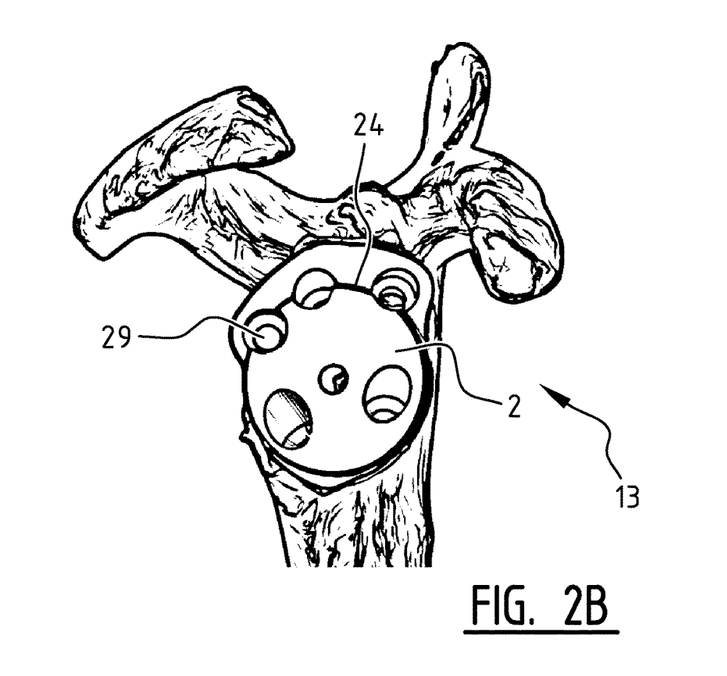

From FIGS. 1b and 2b it is difficult to determine whether the placement of the implant 2 on the glenoid surface 13 is correct. A closer view of FIG. 2b however reveals that a screw hole 29 is not correctly aligned with the bone 1 and is therefore not functional. These kind of misalignments are however difficult to detect in a surgical procedure, as the view is often not clear. A further problem may be that the implant 2 as shown in FIG. 2b may still have a stable fit on the bone 1, despite being misplaced. In other words, although the implant 2 is not correctly placed on the bone 1, the implant 2 may fit the bone 1. This may give the surgeon the idea that the implant 2 is placed correctly.

When FIGS. 1a and 2a are however compared, it is immediately clear that the combination of the guide 3 and the implant 2 is not correctly placed in FIG. 2a. The guide 3 is provided with positioning means in the form of supports 35, 36 which are connected to the base body of the guide 3 by struts 37. Supports 35, 36 engage landmark bone features, in this example the acromion 11 and the coracoid tip and base 12. The surfaces of the supports 35, 36 contacting the bone are formed complementary to the surfaces of the bone for an accurate fit between the guide 3 and the bone 1.

Next to the visual indication of the misplacement as can be clearly seen in FIG. 2a, the surgeon will also notice that the combination of the implant 2 and guide 3 as shown in FIG. 2a will not have a stable fit. This is prevented by the design of guide 3. The guide 3 is designed such that only one possible placement of the combination of guide 3 and implant 2 will result in a sufficiently stable fit.

Figure 3:
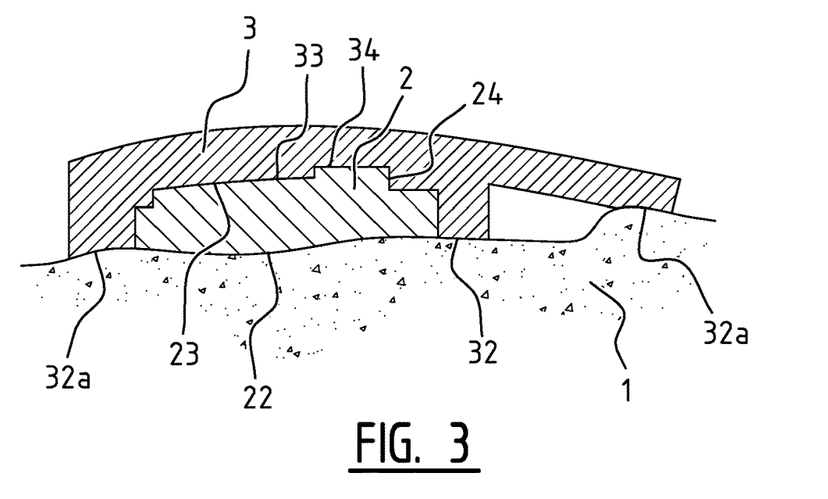
FIG. 3 schematically shows a combination of a guide and implant placed on the bone in cross-section.

Next to the surfaces of the support 35, 36, the guide 3 is hereto provided with bone contacting surfaces 32 and 32a, see FIG. 3. These surfaces 32, 32a which are provided on the side of the guide 3 facing the bone 1 in connected state, are formed complementary to the surfaces of the bone 1 on which they are designed to rest when placed correctly. The combination of the surfaces 32, 32a and the surface 22 of the implant 2 contacting the bone 1, hereby ensure that only one possible stable fit can be achieved between the combination of implant 2/guide 3 on the bone 1. In other words, the combination of surfaces 32, 22, 32a, but possibly also the surfaces of the support 35, 36, only fit the bone 1 in one unique position. As mentioned earlier, the surface 22 of the implant 2 contacting the bone 1 alone does not ensure this unique fit in this example, as also in the situation as shown in FIG. 2b the implant 2 accurately fits the bone 1.

The guide 3 covers the implant 2, wherein the bone contacting surfaces 32 of the guide 3 are located around the implant 2. This provides stability to the combination. The surface 32a placed at a distance further increases the stability and makes it easier to assess whether the combination of guide 3 and implant 2 is placed correctly.

In order to ensure a unique fit between the implant 2 and the guide 3, to ensure the correct placement of the implant 2 when the guide 3 is correctly positioned on the bone 1, the guide 3 and implant 2 are provided with corresponding contact surfaces 33 and 23. The implant contacting surface 33 of the guide 3 is formed complementary to the upper surface 23 of the implant 2. The upper surface 23 of implant 2 is in this example provided with a rim 24 which is received in a corresponding groove 34 in the implant contacting surface 33.

Figure 4:
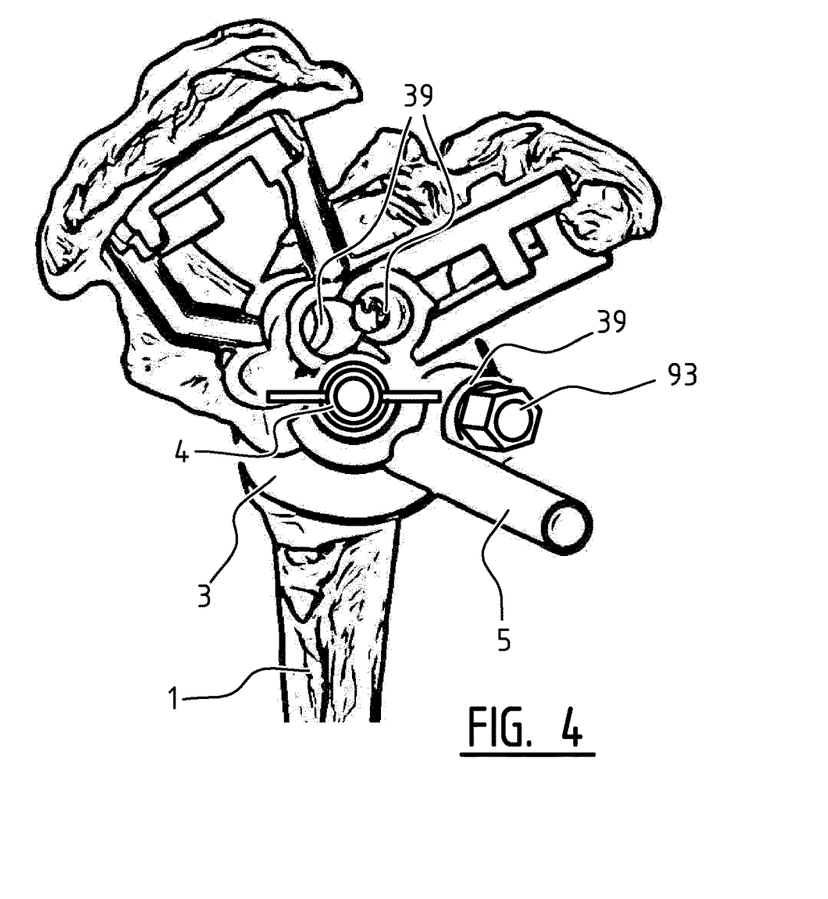
FIG. 4 schematically shows different functional features of the guide.

Next to a guiding function to ensure proper placement of the implant 2 on the bone 1, the guide 3 can also be provided with additional functional features. The guide 3 of FIG. 4 is for instance provided with a handle 5 which can be used by the surgeon to handle the combination of the guide 3 and the implant 2. As the guide 3 can be removed from the implant 2 as will be discussed below, the handle 5 can be relatively large, thereby increasing the user friendliness of the combination.

The guide 3 is further provided with a screw connection 4 for connecting the guide 3 to the implant 2. The implant 2 is hereto provided with a threaded hole which is aligned with a hole in the guide 3. The screw 4 as shown in FIG. 4 is then inserted in the holes and engages the threading of the hole in the implant, thereby releasably connecting the implant 2 to the guide 3. Interconnecting the guide 3 to the implant 2 facilitates placement of the combination on the bone.

Figure 5:
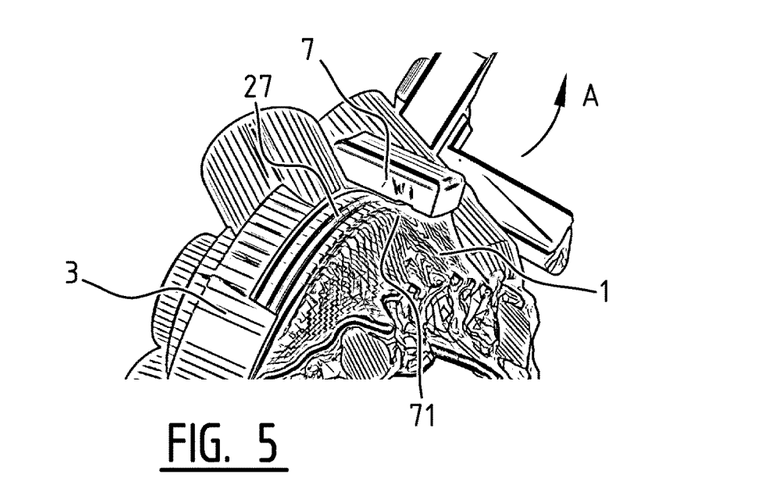
FIG. 5 schematically shows a snap-fit connecting between the guide and the implant.

Another example of an interconnection between the guide 3 and the implant 2 which is placed on the bone 1 is shown in FIG. 5. The guide 3 is provided with a resilient lip 7 which is arranged to engage around an edge 27 of the implant 2. The lip 7 is hereto provided with a hook shaped end 71. For releasing the lip 7 for removing the guide 3 from the implant 2, the lip is moved in a direction indicated with A.

Figure 6A:
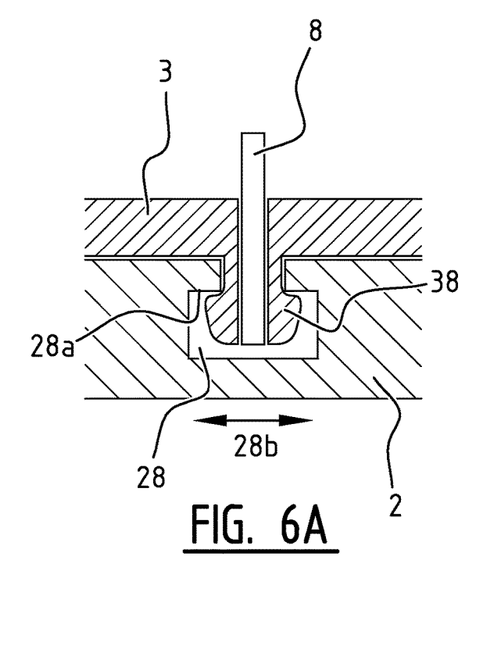
FIGS. 6a and 6b schematically show another connection between the guide and implant in cross-section.
Figure 6B:
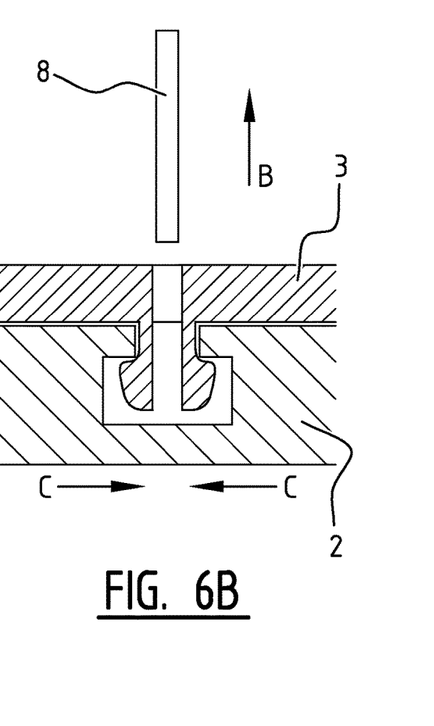

Another variant is shown in FIGS. 6a and 6b. The implant 2 is provided with a blind hole 28 which has a narrowed entry 28a. The guide 3 is provided with resilient protrusions 38 having a through hole for receiving a rod 8. Rod 8 limits movement of the protrusions 38 in direction c, see FIG. 6b. As the outer diameter of the protrusions 38 is larger than the diameter 28b of the entry, the protrusions 38 are locked in the hole 28. When the rod 8 is moved in a direction B, see FIG. 6b, the protrusions 38 are allowed to move in a direction c, such that the outer diameter decreases. The protrusions can now pass through entry 28a and the guide 3 can be removed from the implant 2.

Figure 7A:
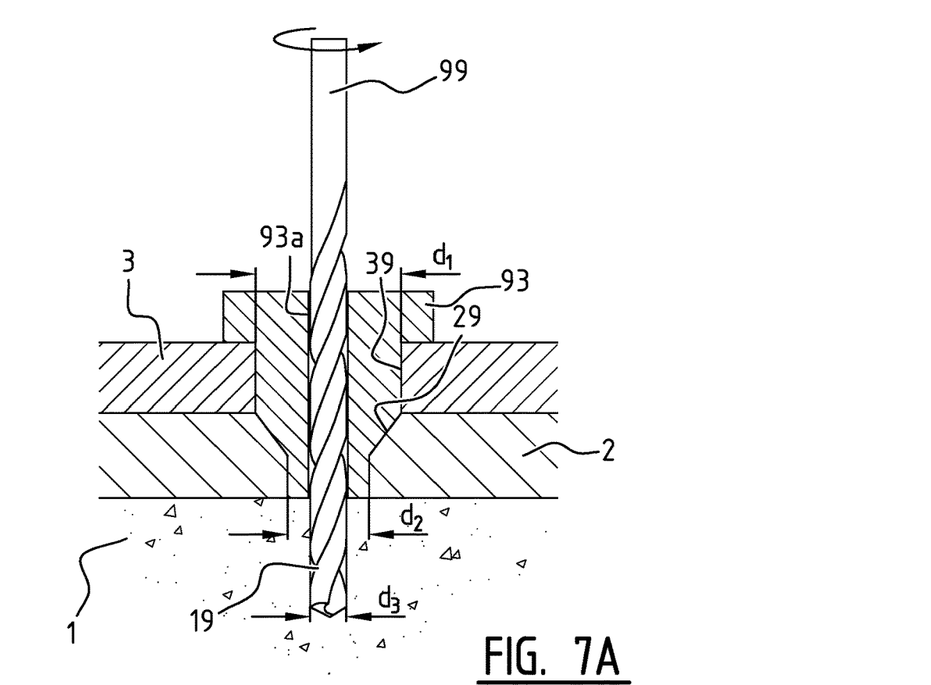
FIGS. 7a and 7b schematically show the process of fixing the implant to the bone with a screw.
Figure 7B:
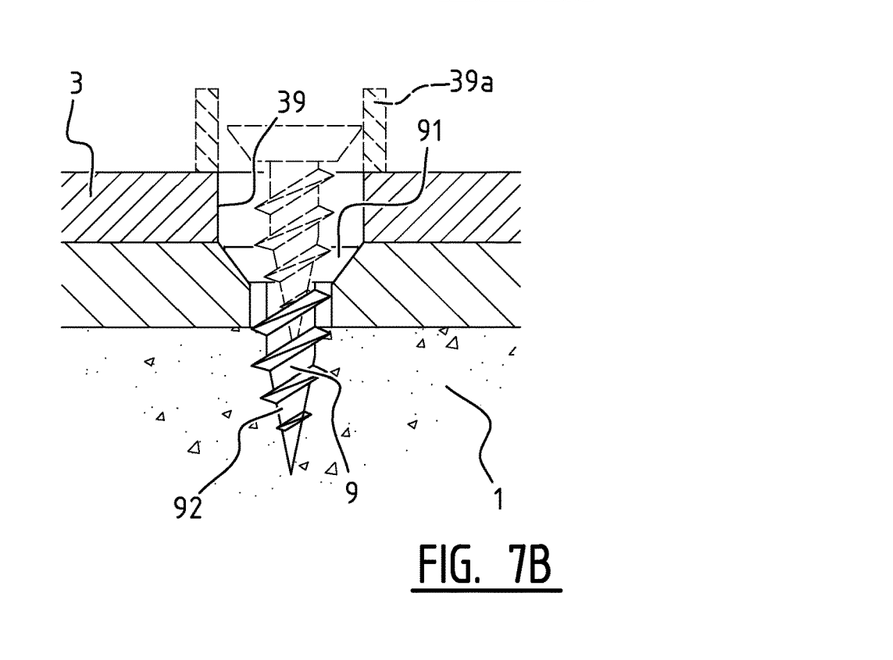

In FIGS. 7a and 7b the procedure of fixating the implant 2 with a bone screw 9 is shown. The guide 3 is hereto provided with a hole 39 which is aligned with a corresponding hole 29 in the implant 2, see also FIGS. 2a and 2b. The hole 39 of the guide 3 has a diameter d1 which is larger than the diameter d2 of the hole 29 of the implant 2. The hole 29 of the implant 2 is further widening towards the side facing away from the bone 1 for receiving the head 91 of the screw 91 as will be explained below. The hole 29 and/or the hole 39 may further be provided with threading.

Inserted in the holes 29 and 39 is a drill cylinder 93 which has an outer surface formed in accordance with the diameters of the holes 29 and 39 such that the drill cylinder 93 fits closely in the holes 29, 39. The outer surface may further be provided with threading cooperating with the treading in the holes 29 and 39 for interconnecting the implant 2 and the guide 3 using the drill cylinder 93.

The drill cylinder 93 has a through hole 93a with a diameter d3 which is smaller than the diameter d2 of the hole 29 of the implant 2. A drill 99 can be inserted in the hole 93a for drilling a hole 19 in the bone 1.

The drill 99 and drill cylinder 93 are then removed and the screw 9 can be inserted. The hole 39 of the guide 3 is dimensioned such that it can receive the head 91 of the screw 9. The diameter of the head 91 of the screw 9 in this example corresponds to the diameter d1 of said hole 39.

Shown in phantom in FIG. 7b is further a flange 39a of the guide 3 located around the hole 39. The inner surface of the flange 39a and the hole 39 hereby form a guiding surface for the screw, also shown in phantom, such that the correct insertion of the screw is ensured. The flanges are also visible as cylinders in for instance FIG. 2a surrounding the holes 39. It is noted that in case the guide 3 is provided with flanges, the drill cylinder 93 is adapted accordingly. It is further possible that a flange 39a is removably connected to the guide 3. The guide 3 and/or flange 39a can hereto be provided with suitable threading.

The head 91 is received in the tapered end of the hole 29 of implant 2 and hereby engages said implant 2, such that the implant 2 is fixed to the bone 1, without fixing the guide 3 to the guide 2 or bone 1. The guide 3 can therefore be removed.

Figure 8A:
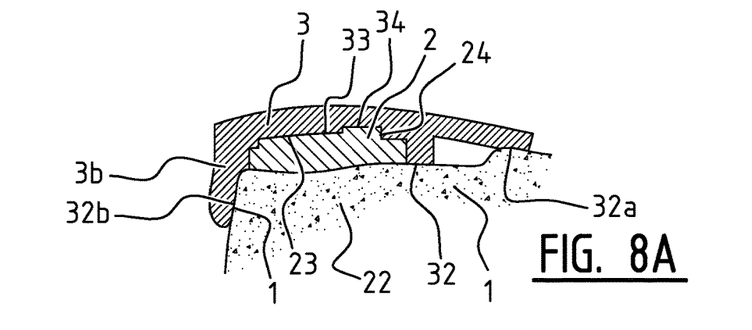
FIGS. 8a and 8b show a further embodiment of the guide.
Figure 8B:
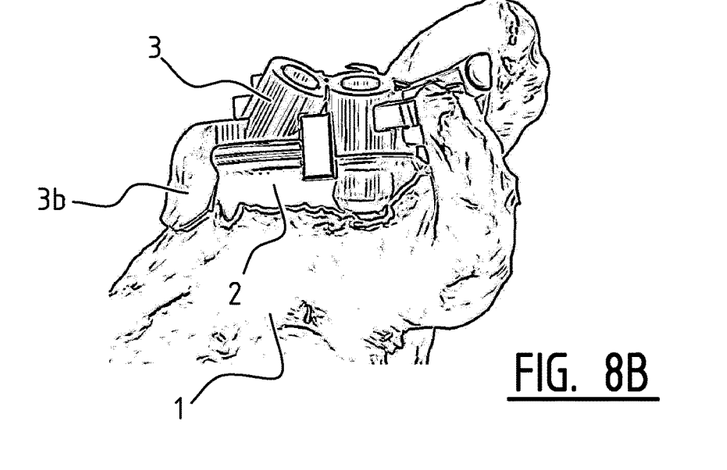

FIG. 8a corresponds to FIG. 3 with the addition that the body is provided with a flange 3b at a lateral side. The flange 3b is provided with a bone contacting surface 32b arranged to contact a side of the bone 1, in this case the lateral border or 'margo lateralis' of the scapula. This improves the stability of the placement and the assessment of the correct placement of the combination. FIG. 8b shows a side view of this situation.

Figure 9:
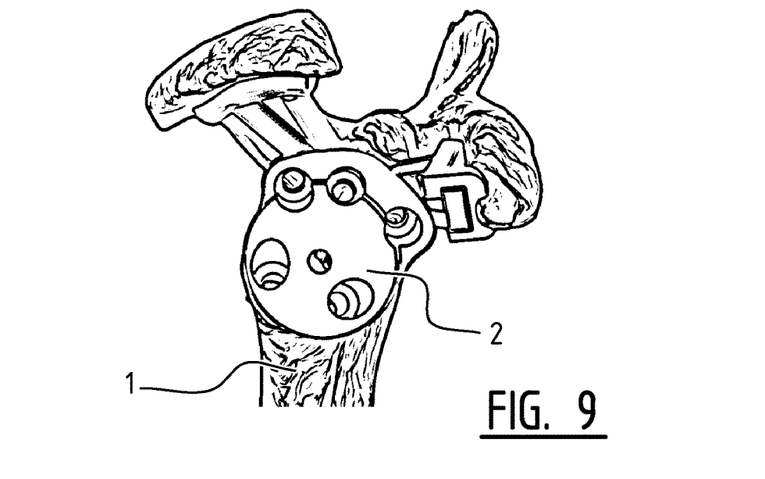
FIG. 9 shows a variant wherein the guide is formed integrally with the implant.

The present invention is not limited to the embodiment shown, but extends also to other embodiments falling within the scope of the appended claims. It may for instance be possible that the guide and the implant are formed integrally, as is shown in FIG. 9.

The invention claimed is:

1. A customized surgical guide for guiding a shoulder implant to a predetermined location on a bone during a surgical procedure, wherein the guide comprises a body comprising at least one implant contacting surface and at least one patient specific bone contacting surface, wherein the implant contacting surface is arranged to contact the implant for ensuring a unique and stable fit between the guide and the implant, and wherein the bone contacting surface is arranged to contact the bone for ensuring a unique and stable fit of a combination of the guide and the implant on the predetermined location on the bone, wherein the guide is provided with a surface of positioning for contacting a bone surface selected from the group consisting of a glenoid neck, a coracoid's base, a coracoid's tip, a lateral border or 'margo lateralis' of a scapula, and an acromion.

2. The customized surgical guide according to claim 1, wherein the implant contacting surface is formed at least partially complementary to a surface of the implant for ensuring the unique fit.

3. The customized surgical guide according to claim 1, wherein the bone contacting surface is formed at least partially complementary to a surface of the bone for ensuring the unique fit.

4. The customized surgical guide according to claim 1, wherein the bone contacting surface of the guide is arranged such that a combination of a bone contacting surface of the implant and said bone contacting surface of the guide together ensure the unique fit.

5. The customized surgical guide according to claim 1, wherein the bone contacting surface of the guide is arranged for ensuring a unique fit of the guide on the bone.

6. The customized surgical guide according to claim 1, further comprising a hole aligned with a screw hole in said implant.

7. The customized surgical guide according to claim 6, wherein the hole in the guide is a screw hole for receiving a screw with a head for fixing the implant to the bone, wherein the diameter of the screw hole in the guide is equal to or larger than the diameter of the screw hole of the implant such that the head of the screw is received in the screw hole of the guide and engages the implant.

8. The customized surgical guide according to claim 7, wherein the guide is provided with a flange surrounding the screw hole and wherein the inner diameter of said flange and the diameter of said screw hole have a diameter corresponding to the diameter of the head of the screw for guiding the screw.

9. The customized surgical guide according to claim 6, wherein the screw hole in the implant is threaded for receiving a drill cylinder provided with corresponding threading.

10. The customized surgical guide according to claim 6, wherein the hole in the guide is a drill hole for receiving and guiding a drill, wherein the diameter of the drill hole is smaller than the diameter of the screw hole of the implant.

11. The customized surgical guide according to claim 1, wherein the bone contacting surface and the implant contacting surface are located on a bone facing side of the body of the guide facing the bone in a connected state.

12. The customized surgical guide according to claim 1, wherein the guide is arranged to contact the implant such that after combining the guide and the implant, the combination of the guide and implant can be uniquely fitted on the bone.

13. The customized surgical guide according to claim 1, further comprises interconnecting means for temporarily interconnecting the guide and the implant during the surgical procedure.

14. The customized surgical guide according to claim 13, wherein the interconnecting means comprises a screw connection and/or a snap-fit connection.

15. The customized surgical guide according to claim 1, further comprising positioning means arranged to facilitate positioning of the combination of the guide and implant on the bone, wherein the positioning means are arranged to engage at least one landmark bone feature on the bone, wherein the positioning means comprise at least one patient specific positioning surface arranged to contact a surface of said landmark bone feature.

16. The customized surgical guide according to claim 1, further comprising a handle extending from the body, wherein the handle is removably attached to the body.

17. The customized surgical guide according to claim 1, wherein the body comprises a flange section provided with a bone contacting surface arranged for contacting a lateral border or 'margo lateralis' of the scapula for ensuring the unique fit.

18. The customized surgical guide according to claim 1 and a bone implant arranged to be implanted on the predetermined location on the bone, wherein the implant has a plurality of possible fits at or near the predetermined location.

19. A method for placing a shoulder implant on a predetermined location on the bone during a surgical procedure, wherein the method comprises the steps of:

providing a shoulder implant;

providing a customized surgical guide for guiding said shoulder implant according to claim 1;

interconnecting said implant and said guide;

placing said combination of the guide and the implant on the predetermined location on the bone;

connecting said implant to the bone; and removing the guide from the implant.

20. The customized surgical guide according to claim 6, wherein the guide further comprises a hole aligned with a screw hole in said implant, wherein the hole in the guide is threaded for receiving a drill cylinder provided with corresponding threading or the hole in the guide is a drill hole for receiving and guiding a drill, wherein the diameter of the drill hole is smaller than the diameter of the screw hole of the implant.

* * * * *